United States Patent [19]

Stone

[11] 4,058,213
[45] Nov. 15, 1977

[54] LOW TEMPERATURE VAPOR PHASE STERILIZATION AND STORAGE OF BIOLOGICALLY ACTIVE INJECTABLE MATERIALS

[76] Inventor: Irwin Stone, 1331 Charmwood Square, San Jose, Calif. 95117

[21] Appl. No.: 702,628

[22] Filed: July 6, 1976

[51] Int. Cl.$^2$ .................... B65B 31/00; A61L 13/00; A61K 31/375
[52] U.S. Cl. .................................. 206/524.4; 21/2; 21/58; 53/22 R; 53/21 FC; 424/280
[58] Field of Search .................. 21/58, 2; 424/280; 53/21 FC, 22 R; 206/524.4

[56] References Cited

U.S. PATENT DOCUMENTS

| 2,283,867 | 5/1942 | Flosdorf et al. | 21/2 UX |
|---|---|---|---|
| 2,832,664 | 4/1958 | Bloch | 21/2 X |
| 2,995,495 | 8/1961 | Pancrazio et al. | 424/280 |
| 3,329,565 | 7/1967 | Speiser et al. | 424/280 X |
| 3,400,199 | 9/1968 | Balassa | 21/58 X |
| 3,615,727 | 10/1971 | Starke | 21/58 |
| 3,618,283 | 11/1971 | Moore et al. | 53/21 FC |
| 3,754,040 | 8/1973 | Moore | 21/58 X |
| 3,908,031 | 9/1975 | Wistreich et al. | 21/58 X |
| 3,936,269 | 2/1976 | Bayne | 21/58 |

*Primary Examiner*—Barry S. Richman
*Attorney, Agent, or Firm*—Steven F. Stone

[57] ABSTRACT

A method for sterilizing solid particulate materials intended to be mixed with a liquid carrier prior to the parenteral or hypodermic introduction into the body of humans and animals. The predetermined amount of particulate material is placed in a sealable container, an amount of ethyl alcohol sufficient to produce a vapor concentration in said container which is toxic to any microorganisms in the particulate material, is added to the container and the container is sealed. When ready for use, the contents of the container may be mixed with sterile water for introduction into the body of humans and animals. This method is particularly useful with materials which tend to decompose when stored as a solution or when exposed to the conditions of normal sterilization procedures and a preferred embodiment involves the sterilization of fine crystalline sodium ascorbate.

4 Claims, No Drawings

LOW TEMPERATURE VAPOR PHASE STERILIZATION AND STORAGE OF BIOLOGICALLY ACTIVE INJECTABLE MATERIALS

BACKGROUND OF THE INVENTION

Conventional sterilization methods for injectable solutions or suspensions generally comprise the exposure of the preformed mixture to high temperatures or ionizing radiation sufficient to kill any microorganisms present. This approach cannot be used with materials that will be adversely affected by the sterilizing conditions. Another approach is the sterile membrane filtration system in which the solution is passed through a sterile Millipore filter system. This technique can be cumbersome, involved and expensive. Both approaches, however, fail to come to grips with the problem associated with solutions which tend to decompose relatively rapidly thereby having an intolerably low shelf life. Such materials as sodium ascorbate, for example, are available in 50 ml vials containing 25% sodium ascorbate solution (12.5 grams sodium ascorbate) preserved with sodium sulfite and benzyl alcohol. When such materials are used, for example, in the treatment of humans and animals in the manner described by F. R. Klenner (J. International Acad. Prev. Med., vol. 1, No. 1, pages 49-65 (1974) and W. O. Belfield et al (J. International Acad. Prev. Med., vol. 2, No. 3, pages 10-26 (1975), and E. Cameron et al, J. Internat. Res. Commun., vol. 1, No. 6, pages 38 (1973), the sulfite produced adverse side effects resembling those of beri-beri as a result of the reaction of the sulfite with the patient's vitamin $B_1$. The manufacturer, upon request, has produced vials without the sulfite but the manufacturer believes the shelf life is so short that they do not distribute the product through normal channels. What is needed is an inexpensive means for sterilizing sensitive materials in the solid state so that they can be stored for long periods and mixed with sterile water immediately prior to use. This invention describes such an approach.

It is accordingly an object of this invention to provide a simple economical method for sterilizing sensitive solid materials.

It is another object of this invention to provide a sterile container of a sensitive solid material.

A further object of this invention is to provide sterilization with a non-toxic, volatile sterilizing agent that does not have to be removed from the mixture before use, and in the quantities employed for sterilization it would be normally metabolized by the body without any unfavorable side effects on injection.

These and other objects of this invention will be readily apparent from the following description.

DESCRIPTION OF THE INVENTION

According to this invention a stable sterile particulate solid material is prepared by a simple, non-toxic, inexpensive means in a convenient cheap disposable container. The container and contents has a long shelf life and is capable of being simply and rapidly used by the physician or nurse in the preparation of fresh injectable solutions immediately before injection into the patient.

The following description will be directed to the preferred embodiment of sodium ascorbate, but it should be recognized that the invention can be used with combinations of sodium ascorbate with other materials or with any other pharmaceutical material (without the presence of sodium ascorbate), that is non-reactive with ethyl alcohol.

Sodium ascorbate, for example, is rather unstable to heat both in the dry state and in solution, so that the temperatures required for heat sterilization causes destruction and loss of activity of the ascorbate. Sterilization by sterile membrane filtration through a completely sterile system such as that manufactured by the Millipore Corporation can be done, but is limited to solutions. This is an expensive and time consuming operation, especially if it is necessary to first get the sodium ascorbate into solution, membrane filter this solution and then freeze-dry the sterile solution under sterile conditions to obtain a sterile dry powder for permanent shelf life stability in the dry state in the sterile packaged product.

Another method of sterilization, by high energy radiation, requires a tremendous investment in special equipment and there is no data available on the effect of such high energy radiation on an unstable material like sodium ascorbate as to loss in activity and the shelf life stability of radiated ascorbate.

I have overcome all these objections to present customary sterilization procedures by the provision of a very simple, elegant and inexpensive, non-toxic procedure for the low-temperature, vapor phase sterilization, which produces a stable particulate material suitable for injection purposes, with no loss of activity.

The principle of the method is to place a weighed charge of, for example, sodium ascorbate (fine crystals preferred) into a suitable sealable container (glass, plastic or other) and add a quantity of ethyl alcohol sufficient to produce a high enough concentration of alcoholic vapor to effectively kill and inactivate any viable microorganisms adhering to the sodium ascorbate during the shelf-life storage time of the package containing it. At the time the physician or nurse wants to prepare the solution for injection, they either remove or penetrate the seal with a sterile hypodermic syringe and add the required amount of sterile water for injection needed for the prepartion of the solution. The sodium ascorbate quickly dissolves and the solution is ready for injection into the patient or for further dilution for parenteral drip therapy. No attempt is made to remove the ethyl alcohol as the amount originally added is so small and harmless and will be normally metabolized after injection into the patient, with no deleterious side effects or toxicity. The patient is thus assured a perfectly fresh solution of the proper ascorbate strength as the time between preparation and administration is so short that no loss of ascorbate activity can take place.

The amount of ethyl alcohol required in this treatment is very small and is easily calculated from the volume of the container and the fact that 100 milligrams of ethyl alcohol alcohol (100%) will produce approximately 50 milliliters of saturated vapor at room temperature. If a 6 ounce (170 ml) container is used, then about 360 milligrams of ethyl will be required to fill the container with ethyl alcohol vapor. Less quantities than that giving 100% saturation, like 50% saturation, will also be effective, but I prefer to use an amount giving about 150% saturation. Substantially larger amounts of ethyl alcohol beyond about 150% are unnecessary and only add to the costs. The amounts of ethyl alcohol needed are so small that they do not "wet" the powder, with visible liquid in the interstices of the particulate materials. Besides, keeping the ethyl alcohol levels minimal is desirable, to avoid unnecessary increases in the alcohol blood levels of the patients. The adult blood volume is about 4 liters so the ethyl alcohol added in the above example would produce an insignificant rise of about 0.01% in the alcohol blood level.

The ethyl alcohol concentration in the alcohol liquid added to the dry particulate material is not critical, but should be preferably high to avoid adding excessive water to the mixture along with the alcohol. 100% or absolute alcohol may be employed, but the less expensive azeotropic concentration of about 95% ethyl alcohol is preferred. Lesser concentrations can be used but require more liquid to generate the required vapor volumes.

The costs of the finished sterile product of this invention will be low, being not much more than the costs of the raw materials and package, as there are no involved expensive processing operations to produce sterility. This results in substantial savings to the patient in the cost of medical care.

Other materials like soluble vitamins, minerals or other drugs that are required to be injected along with the ascorbate may be added to the sodium ascorbate in the package and the ethyl alcohol added to the mixture before the package is sealed. In this way the other additives for injection are sterilized at the same time as the sodium ascorbate.

Sterile water "For Injection" is the preferred liquid for dissolving the treated sodium ascorbate of this invention. I have found that if this injectable grade of water is not available, particularly in veterinary medicine, boiled and cooled distilled water or even plain tap water may be used for dilution, without harmful effect on the patient.

The following are typical examples of the procedure of this patent:

EXAMPLE 1

Into a clean 6 ounce screw capped bottle wiegh 15 grams of sodium ascorbate fine crystals. Add 360 milligrams of ethyl alcohol (0.46 ml 95% ethyl alcohol), seal tightly and shake vigorously to distribute the alcohol and permit rapid vaporization throughout the sealed bottle. Allow to stand.

EXAMPLE 2

Weigh 30 grams of sodium ascorbate into a dry 1 liter plastic parenteral bag. add 600 milligrams of ethyl alcohol (0.8 ml of 90% ethyl alcohol) and mix thoroughly with the contained powder. Fold the bag and store flat (to limit the internal volume) until ready to use. Dilute with 1 liter of sterile water "For Injection", immediately before connecting to the patient. This will produce a fresh sterile isotonic parenteral solution of sodium ascorbate suitable for continuous intravenous drip therapy.

EXAMPLE 3

Weigh 20 grams of sodium ascorbate (fine crystals) into a 100 ml sealable vial and add 300 milligrams of ethyl alcohol (0.48 ml 70% ethyl alcohol). Shake thoroughly and seal with a closure that can be sterily penetrated by a hypodermic needle. Allow to stand. When ready for use, draw 100 ml of sterile water for injection into a sterile hypodermic syringe. Penetrate the cap with the hypodermic needle and add sufficient water to dissolve the sodium ascorbate by swirling, without removing the hypodermic from the vial. When dissolved the solution is sucked back into the hypodermic syringe, mixed and is ready for injection.

EXAMPLE 4

10 grams of sodium ascorbate (fine crystals) are weighed into a 100 ml sealable vial and 300 milligrams of ethyl alcohol is added (0.38 ml absolute alcohol) and the vial is sealed and shaken as in Example 3 and is handled similarly.

While this invention has been disclosed with respect to specific embodiments, it is not limited thereto. Various modifications can be made without departing from the scope of the invention which is limited only by the following claims wherein:

I claim:

1. A method for sterilizing and storing a biologically active particulate solid material adapted for injection into a patient which comprises:
    a. placing a charge of the material in a sealable container
    b. adding to said container an amount of ethyl alcohol sufficient to produce a sterilizing ethyl alcohol vapor in said container
    c. sealing said container and
    d. storing said sealed container for a period of time at least sufficient to sterlize said material.

2. The method of claim 1 wherein said solid material comprises sodium ascorbate.

3. An article of manufacture comprising a sealed disposable container containing an amount of biologically active solid particulate material adapted for injection into a patient and an amount of ethyl alcohol sufficient to generate a sterilizing vapor of ethyl alcohol in said container.

4. The article of claim 3 wherein said biologically active material comprises sodium ascorbate.

* * * * *